United States Patent [19]
Ludvigsson et al.

[11] Patent Number: 5,205,743
[45] Date of Patent: Apr. 27, 1993

[54] DENTAL TREATMENT METHOD

[75] Inventors: Björn M. Ludvigsson, Örviken; Ulf D. L. Strömberg, Gothenburg, both of Sweden

[73] Assignee: Boliden Contech AB, Stockholm, Sweden

[21] Appl. No.: 822,912

[22] Filed: Jan. 21, 1992

[30] Foreign Application Priority Data

Feb. 7, 1991 [SE] Sweden .................................. 9100380

[51] Int. Cl.$^5$ .......................... A61C 17/06; A61C 17/14
[52] U.S. Cl. .......................................... 433/92; 433/91
[58] Field of Search .............................. 433/92, 91, 95

[56] References Cited

U.S. PATENT DOCUMENTS

| | | | |
|---|---|---|---|
| 3,735,491 | 5/1973 | Pabalan, Jr. | 433/93 |
| 3,786,619 | 1/1974 | Melkersson et al. | 55/72 |
| 4,252,054 | 2/1981 | Bakels | 98/115.3 |
| 4,460,340 | 7/1984 | Stark et al. | 433/91 |
| 4,975,057 | 12/1990 | Dyfvermark | 433/93 |
| 5,018,971 | 5/1991 | Trawoger et al. | 433/92 |

FOREIGN PATENT DOCUMENTS

| | | |
|---|---|---|
| 284641 | 10/1988 | European Pat. Off. . |
| 333673 | 9/1989 | European Pat. Off. ............. 433/92 |
| 2150592 | 8/1979 | Fed. Rep. of Germany . |

Primary Examiner—Gene Mancene
Assistant Examiner—Cindy A. Cherichetti
Attorney, Agent, or Firm—Burns, Doane, Swecker & Mathis

[57] ABSTRACT

The invention relates to a method of decreasing the risk of injury from mercury in conjunction with dental treatment. The invention is characterized by passing an effective air flow immediately outside the oral cavity in which the dental treatment is effected. The air flow, together with air removed by suction from the oral cavity when sucking saliva therefrom is passed through a first filter in which solid and liquid particles are extracted from the air flow. The air is then passed through a second filter which is capable of taking up essentially all of the mercury vapor present in the air. This filter is preferably a selenium filter.

13 Claims, 1 Drawing Sheet

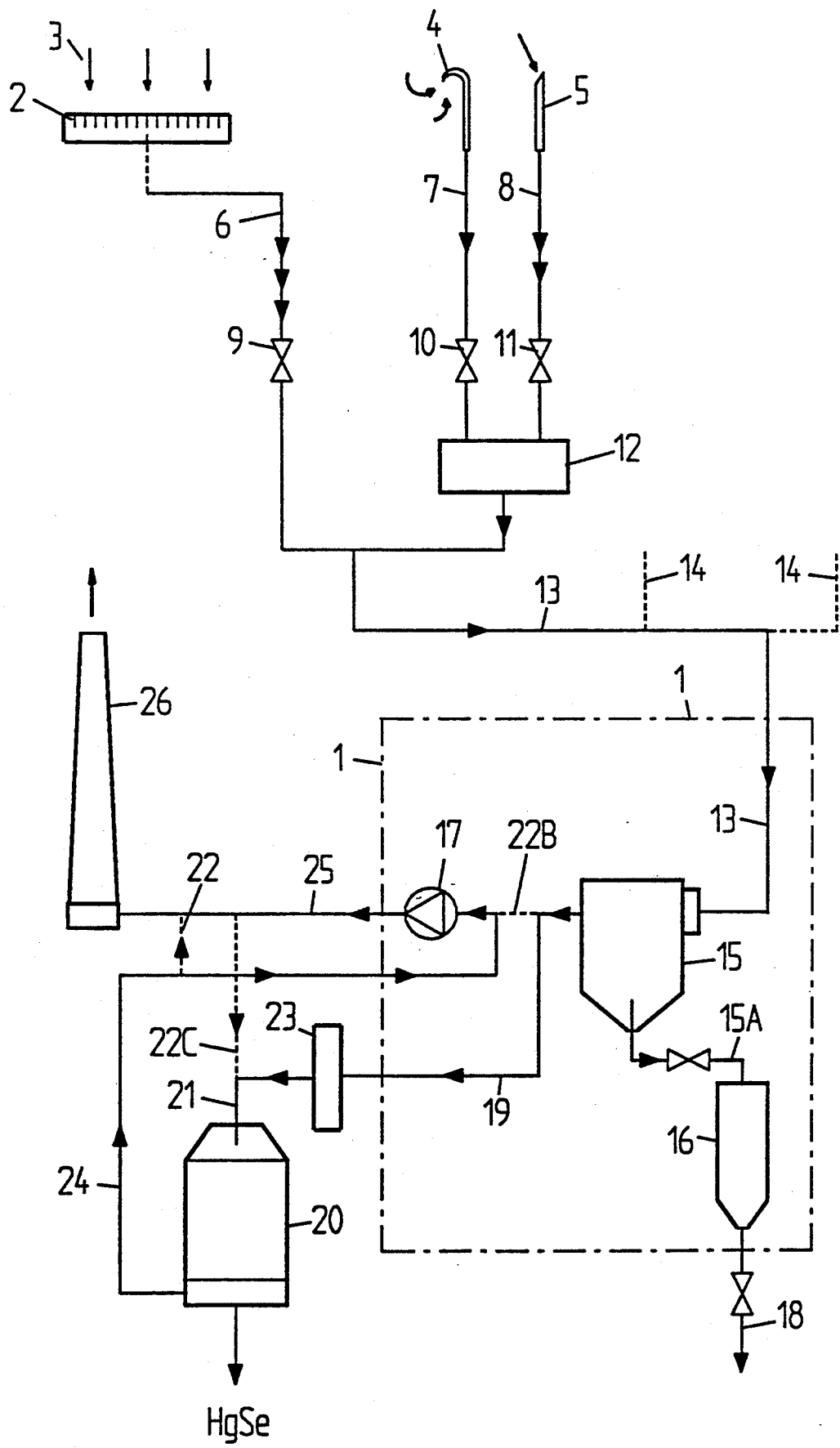

DENTAL TREATMENT METHOD

The present invention relates to a method of reducing the risk of injury by mercury contamination in conjunction with dental treatment.

Mercury is one of the most dangerous substances that we come into contact with in the course of our daily lives. This is because mercury, in addition to being highly toxic, has a high vapour pressure even at normal ambient temperatures. The limits of working hygiene are exceeded even at temperatures far beneath 0° C., when mercury is allowed to vaporize in a room. Mercury vapour is odorless, invisible and is readily absorbed by both skin and mucous membrane, mucosa. Thus, it can be said without exaggeration that mercury is one of the most treacherous of known poisons and also the most difficult to safeguard against. Thus, all those who come into contact with mercury find themselves in a risk zone, including dental personnel who use or have used amalgam for teeth fillings in the course of their work. When amalgam is drilled, mercury vapour is formed in an amount which depends in part on the type of amalgam concerned. Discussions which have been carried out publicly with regard to the toxicity of amalgam have naturally caused more and more people to ask for their old amalgam fillings to be replaced with a less harmful material, this treatment often being referred to a so-called amalgam decontamination. It has been discovered that such mercury decontamination processes are far from being without risk to the patient, because of the mercury that is released during the decontamination process. The dental personnel involved in the decontamination process also, of course, stand at high risk when a larger number of such processes are carried out in one and the same dental surgery. It has been found that the health of many patients has deteriorated radically in conjunction with amalgam decontamination processes, and in the case of certain groups who suffer from specific illnesses the exposure to mercury during the contamination process can cause permanent damage.

Efforts have been made to reduce the risks involved when handling amalgam, including the process of amalgam decontamination. For example, equipment is available which will handle and collect solid waste from the oral cavity in dental work which includes amalgam. The waste is drawn by suction through a saliva tube or by a fast rotating intensive suction device which is used intermittently and inserted into the oral cavity from time to time in order to remove by suction saliva and solid waste residues resulting from the dental treatment in progress. Also available are so-called hygiene suction devices which are intended to remove air from the patient's oral cavity by suction. The extremely fine particles, for instance the extremely fine amalgam residues, liquid droplets and even virus particles present in this air are then extracted therefrom with the aid of a particle-capturing filter. Filters having the ability to capture particles down to a size of 0.2 micron can be constructed.

Equipment of this type will naturally reduce the risk of subjecting patient and dental personnel to the immediate effect of the mercury released during the dental treatment in progress.

However, even though mercury vapour is transported away from the patient and the dental personnel when using such equipment, the filters used fail to capture the mercury vapour effectively, irrespective of the sophistication of the filter used. Mercury vapour that is generated during the dental treatment in progress will therefore pass through the filter and into the ambient surroundings, either in the actual room itself or to locations outside said room and there accumulate. Furthermore, the mercury vapour generated from the material captured in the filter is spread successively into the outer environment by the air passing through the filter and therewith further increases the emission of mercury in the environment. This may, of course, constitute a serious problem, because of the risk of the emission of mercury vapour into the dental facilities, and therewith constitute a secondary environment threat to both patients and dental personnel. No large emissions of mercury vapour to the external environment should be permitted in the future, either through ventilation of the localities concerned or by immediate release of air from particle filters.

The object of the present invention is to prevent the harmful effects of mercury, thereby eliminating the aforementioned problems.

In accordance with the present invention, an effective flow of air is caused to pass in the immediate vicinity of the oral cavity in which dental treatment is carried out. This air flow, together with air accompanying saliva that is sucked from the interior of the oral cavity during the treatment under progress, is passed through a first filter in which particles, including liquid droplets, are extracted from the air. The air is then passed through a second filter which is capable of absorbing essentially all mercury vapour present in the air.

By an "effective" air flow is meant an air flow which is so adapted that all mercury, both in vapour form and in the form of amalgam dust, released and generated during the treatment process is prevented from reaching the patient and the dental personnel and also from entering the ambient air, by forcing these contaminants to follow the air flow through the filters.

Essentially all of the mercury vapour carried by the air flow is absorbed with the aid of a selenium filter. Such filters can be constructed so as to take-up practically 100% of the mercury vapour present. Selenium filters of this kind are described and illustrated, for instance, in U.S. Pat. No. 3,786,619. These filters contain a cleaning material which includes selenium, selenium sulphide or other selenium compounds or mixtures thereof as its active component. These active components may be applied to an inert carrier of silica, aluminium oxide, iron oxide, ceramic material or mixtures thereof. Other effective, mercury vapour capturing filters may also be used, for example carbon filters of the kind described and illustrated in DE-B 21 50 592, these filters containing active carbon which has been impregnated with sulphur or sulphur compounds, by treating the carbon with $SO_2$ or $H_2S$ or by successively treating the carbon with $H_2S$ and $SO_2$ or $SO_2$ and $H_2S$ such as to form solid sulphur or sulphur compounds.

In order to reduce the risk of the selenium or carbon filters becoming blocked, the air is preferably dried before it is passed into the filters, this drying process also including raising the temperature of the air so as to reduce the risk of condensation and the blocking of the mercury filter by the slurry formed in the event of such condensation.

It has been found that an air flow rate from 500–2,000 liters/min. will provide an effective air flow suitable for the purpose intended.

When using selenium filters, mercury is taken up by the selenium layer on the carrier material to form mercury selenide according to the formula:

$$Hg + Se \rightarrow HgSe$$

The mercury selenide formed is a highly stable compound of extremely low solubility and low vapour pressure at ambient temperatures. Mercury selenide can therefore be handled safely without risk of the mercury being released either to atmosphere or to any aqueous environment. As an illustrative example of the stability of HgSe, it can be mentioned that about 300,000 m$^3$ water, corresponding to the content of about 75 standard 50-meter swimming pools, is required to release one single atom of mercury from a teaspoonful of solid HgSe.

BRIEF DESCRIPTION OF THE DRAWING

The invention will now be described in more detail with reference to the accompanying drawing. The single Figure is a schematic flowsheet illustrating the manner in which a preferred embodiment of the inventive method is carried out.

DETAILED DESCRIPTION OF THE PREFERRED EMBODIMENT

Shown in the drawing is a central suction unit 1 to which there is connected an oral-cavity suction device 2 which is intended to be attached to the patient so as to provide an air flow in the oral cavity or in the vicinity of the oral cavity, this air flow being illustrated by arrows 3. Also connected to the central suction device 1 is a low-speed first saliva suction device 4 and a high-speed second saliva suction device 5. The system also includes regulating devices 9, 10, 11 by means of which the air flows in respective connections 6, 7 and 8 between the oral-cavity suction device 2 and respective saliva suction devices 4 and 5 and the central suction unit 1 can be adjusted.

A course filter 12 is provided for extracting coarse particles from the suction devices 4, 5. The combined air flows 6, 7, 8 are passed through a conduit 13 to the central suction unit 1. Several treatment locations can be connected to the central unit 1, as indicated by the broken lines 14. The central suction unit 1 comprises a liquid separator 15, an amalgam separator 16 and a vacuum pump 17, by means of which a negative pressure or vacuum of 18→20 kPa (0.18-0.20 atm) is maintained in the system. In the central unit 1, the air flow is first cleansed in a particle-and-liquid separator 15, in which solid particles, for instance amalgam and tooth residues, and liquid droplets, for instance water and mercury droplets, are extracted from the air flow. The extracted material is passed through a conduit 15A to a so-called amalgam separator 16, from which liquid that has been cleaned with respect to amalgam and other solid material is passed to an outlet, as indicated by an arrow 18. The air flow from the liquid separator 15 is then passed through a conduit 19 to a selenium filter 20, which in the illustrated embodiment is connected to the central suction unit 1 between the separator 15 and the vacuum pump 17. As indicated by the broken lines 22, 22B, 22C, which illustrate the alternative conduit arrangement, the filter 20 may also be connected downstream of the vacuum pump 17. The air flow passes through a droplet separator 23 prior to being passed to the selenium filter 20. The selenium filter 20 extracts essentially all of the mercury vapour carried by the treated air flow, to form solid HgSe, which can be taken out, suitable intermittently, for instance when removing the filter content and regenerating the filter. The air flow passes from the selenium filter 20 through a conduit 24, the pump 17, and through a conduit 25 to atmosphere, optionally via a ventilation system, here illustrated by a chimney 26. Since the air flow in the conduit 25 is essentially free from toxic or otherwise harmful waste, the air can be safely released to atmosphere.

The inventive method provides obvious advantages. For example, the method is relatively inexpensive, since existing dental suction and hygiene systems for recovering solid amalgam residues can be readily supplemented with means for achieving essentially total protection with regard to mercury. The invention also enables all mercury to be dealt with, irrespective of whether the mercury is in elemental form, gaseous form or liquid form or is present in the form of solids or liquid-forming compounds or alloys.

We claim:

1. A method of reducing the risk of injury from mercury in conjunction with dental treatment comprising passing an air flow immediately outside an oral cavity in which the dental treatment is taking place; passing the air flow, together with air removed by suction from the oral cavity when removing saliva by suction during the dental treatment, through a first filter for extracting solid and liquid particles from said air flow; and passing the air flow through a second filter which comprises a selenium filter so that essentially all of the mercury vapor is adsorbed on the selenium filter.

2. The method of claim 1 wherein the air flow is heated prior to passing the air flow through the second filter.

3. The method of claim 2 wherein the air flow is from 500 to 2,000 liters per minute.

4. The method of claim 1 wherein the air flow is dried prior to passing the air flow through the second filter.

5. The method of claim 4 wherein the air flow is from 500 to 2,000 liters per minute.

6. The method of claim 1 wherein the air flow is from 500 to 2,000 liters per minute.

7. A method of reducing the risk of injury from mercury in conjunction with dental treatment comprising passing an air flow immediately outside an oral cavity in which the dental treatment is taking place; passing the air flow, together with air removed by suction from the oral cavity when removing saliva by suction during the dental treatment, through a first filter for extracting solid and liquid particles from said air flow; drying or heating the air; and passing the air flow through a second filter which is capable of adsorbing essentially all of the mercury vapor in the air flow.

8. The method of claim 7 wherein the air flow is heated prior to passing the air flow through the second filter.

9. The method of claim 8 wherein the air flow is from 500 to 2,000 liters per minute.

10. The method of claim 7 wherein the air flow is dried prior to passing the air flow through the second filter.

11. The method of claim 10 wherein the air flow is from 500 to 2,000 liters per minute.

12. The method of claim 7 wherein the second filter is a selenium filter.

13. The method of claim 12 wherein the air flow is from 500 to 2,000 liters per minute.

* * * * *